United States Patent [19]

Nichols

[11] 4,181,297
[45] Jan. 1, 1980

[54] POSITIONING DEVICE FOR HUMAN LIMBS AND THE LIKE

[76] Inventor: Thomas K. Nichols, Box 760A, R.D. #2, Andover, N.J. 07821

[21] Appl. No.: 851,867

[22] Filed: Nov. 16, 1977

[51] Int. Cl.² .................... A61G 13/00; A61F 13/00; F16C 11/00
[52] U.S. Cl. ................ 269/328; 128/132 R; 128/134; 403/61
[58] Field of Search .............. 128/82, 83, 88, 89 R, 128/20, 132 R, 132 D, 133, 134, 135; 269/322, 328; 403/61

[56] References Cited

U.S. PATENT DOCUMENTS

| 908,751 | 1/1909 | Cooke | 403/61 |
|---|---|---|---|
| 1,447,565 | 3/1923 | Nosan | 403/61 |
| 1,748,227 | 2/1930 | Hyams | 128/346 |
| 1,799,781 | 4/1931 | Chalfont | 27/31 |
| 2,199,949 | 5/1940 | Davis | 27/23 |
| 2,207,968 | 7/1940 | Brasure | 27/1 |
| 2,266,230 | 12/1941 | Mazzeo et al. | 128/327 |
| 2,535,559 | 12/1950 | Wolf | 269/328 |
| 2,614,558 | 10/1952 | Lovell | 128/83 UX |
| 3,823,709 | 7/1974 | McGuire | 128/20 |
| 3,835,861 | 9/1974 | Kees, Jr. et al. | 269/328 |
| 3,844,550 | 10/1974 | McGuire | 269/328 |
| 4,045,678 | 8/1977 | Rickard | 269/328 |

OTHER PUBLICATIONS

Frank Sholz X-Ray Corp. Catalogue, p. 146, not dated, P.O. Box 223, Needham Heights, Mass. 02194.

Primary Examiner—Robert W. Michell
Assistant Examiner—C. W. Shedd
Attorney, Agent, or Firm—Richard D. Weber

[57] ABSTRACT

A positioning device for holding a human limb in a fixed position on a table for examination and/or X-ray photography. The device secures the limb against movement in any direction and is thus particularly adapted for stress arthrogram examinations. A lever actuated suction cup assembly selectively positionable on a table carries a horizontal limb support plate in spaced relation above the table. A pair of opposed upstanding clamp assemblies are slidably mounted on the support plate and are selectively adjustable into a fixed clamping position in engagement with a human limb placed therebetween on the support plate. The limb engaging surfaces of the clamp assemblies have a concave configuration and are selectively angularly adjustable to accommodate the taper of the secured limb.

13 Claims, 10 Drawing Figures

POSITIONING DEVICE FOR HUMAN LIMBS AND THE LIKE

BACKGROUND OF THE INVENTION

The present invention relates generally to positioning devices and more particularly to a device for clamping a human limb or the like in a fixed position on a table surface for examination, X-ray photography or other procedures. Although the device is adaptable for a variety of uses, it has primarily been developed for use in securing a patient's leg during stress arthrogram examinations of the knee.

In a stress arthrogram examination, the knee is injected with a fluid (dye) under pressure which enhances the definition of the knee elements and particularly damaged or dislocated portions thereof when viewed with a fluoroscope or on X-ray film. In the usual procedure, the patient is placed in either a prone or supine position on an examination table with the knee located beneath a fluoroscope screen and an X-ray machine. Following injection of the pressurized fluid into the knee, the lower leg is manipulated to arrange the knee elements into the desired relationship as viewed through the fluoroscope to reveal the problem areas. X-rays are then taken with the knee stressed to provide the most revealing pictures.

During such arthrogram examinations, it is important that the knee be maintained in as close proximity as possible to a particular place on the table so that the fluoroscope and X-ray equipment need not be repositioned. It is further necessary that some means be provided to restrict movement of the patient's thigh while stress is placed on the lower leg. Prior to the present invention, the most commonly used device to position and restrain the patient's leg has been a bracket which attaches to the edge of the examination table, extends along the table surface and terminates in a vertical arm against which one side of the patient's thigh is placed. Such an arrangement has several drawbacks. The bracket being attached to the edge of the table can only give support to the leg a fixed distance from the table edge and it must be removed and transferred to the opposite side of the table should the other leg be examined. The bracket further provides support against only one side of the leg and does not prevent vertical leg movement. Furthermore, the bracket is normally suited for only one type of table because of its table edge attachment. Since most hospitals have several types of examination tables having either flat or slightly concave table surfaces, the conventional position devices cannot be interchangeably used.

A further consideration is the importance of completing the examination as expeditiously as possible. Not only is the injection of the fluid and the subsequent manipulation of the leg painful to the patient, but the dye effect of the fluid is temporary. Furthermore, the doctor's time is valuable as is the time of use of the examination facilities.

SUMMARY OF THE INVENTION

In the present invention, a positioning device is provided which permits the rapid and secure positioning of a limb such as a leg on an examining table at any desired location on the table. The device in brief comprises a lever actuated suction cup assembly on which is mounted a horizontal limb support plate in spaced relation above the table. A pair of opposed upstanding clamp assemblies having concave limb-engaging surfaces are slidably mounted on the support plate and are selectively adjustable into a fixed clamping position in engagement with a limb placed therebetween on the support plate. A ratchet type locking mechanism is preferably employed to automatically lock the clamp assembly in the desired clamping position against the limb. The limb engaging surfaces of the clamp assemblies have a concave configuration and are selectively angularly adjustable to accommodate the taper of the secured limb. The device secures the limb against movement in any direction and is thus particularly adapted for stress arthrogram examinations. The suction cup assembly permits the quick attachment of the device to any examination table at any desired location on the table. The adjustable spacing of the clamp assemblies and the angular adjustment of the clamp members permit a rapid setup of the device regardless of the type of table or the size and shape of the patient's limb.

It is accordingly a primary object of the present invention to provide a positioning device for firmly securing a human limb and especially a human leg to a supporting surface such as an examining table.

A further object of the invention is to provide a positioning device as described which may be quickly and easily applied, removed, or repositioned on the table surface.

Another object of the invention is to provide a positioning device as described which is adapted to mounting on any type of examination table.

Still another object of the invention is to provide a positioning device as described which is selectively adjustable to accommodate limbs of different size and shape.

A still further object of the invention is to provide a positioning device as described which permits stress to be applied to the limb in any direction with a single setup of the device.

Still another object of the invention is to provide a positioning device as described which is self-contained, requiring no tools, screws, etc. for setup, and which is simple to operate.

Additional objects and advantages of the invention will be more readily apparent from the description of the drawings and the preferred embodiment set forth below.

DESCRIPTION OF THE PREFERRED EMBODIMENT

Figure 1:
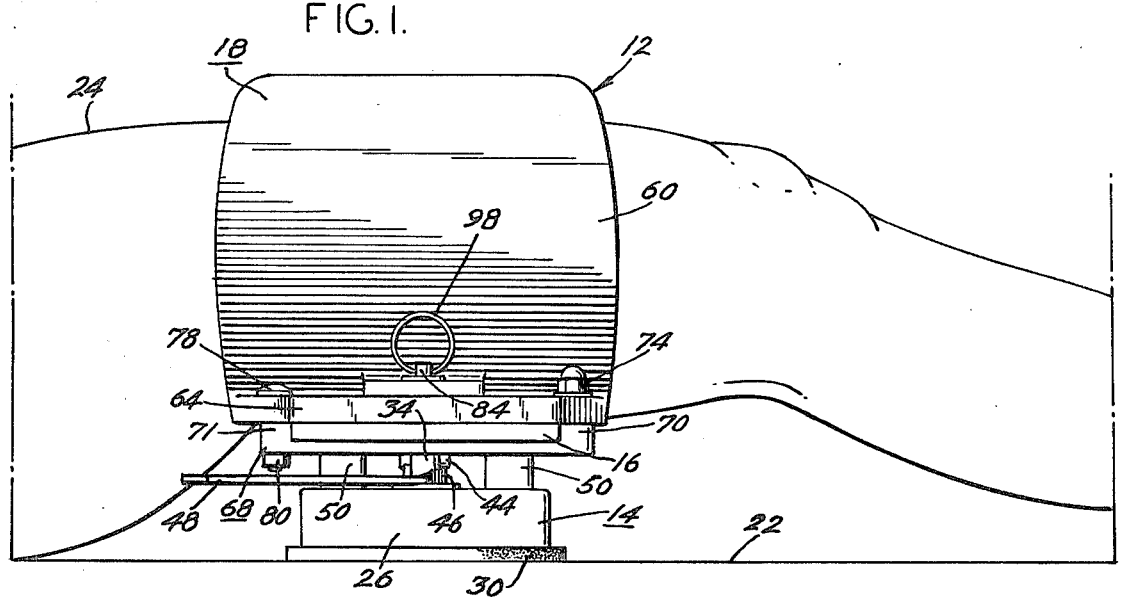
FIG. 1 is a side elevational view of a positioning device in accordance with the present invention shown clamping a human thigh in a predetermined position above a table surface.

Referring to the drawings, a positioning device generally designated 12 in accordance with the present invention comprises in general a suction cup assembly 14, a limb support plate 16 carried by said cup assembly 14, and opposed upstanding clamp assemblies 18 and 20 slidably disposed on said support plate 16. As shown in FIG. 1, with the suction cup assembly secured to a table surface 22, a human leg 24 and specifically the thigh portion thereof may be supported on the support plate 16 and clamped between the opposed clamp assemblies 18 and 20 to hold the thigh in a predetermined position during examination of the knee.

Figure 4:
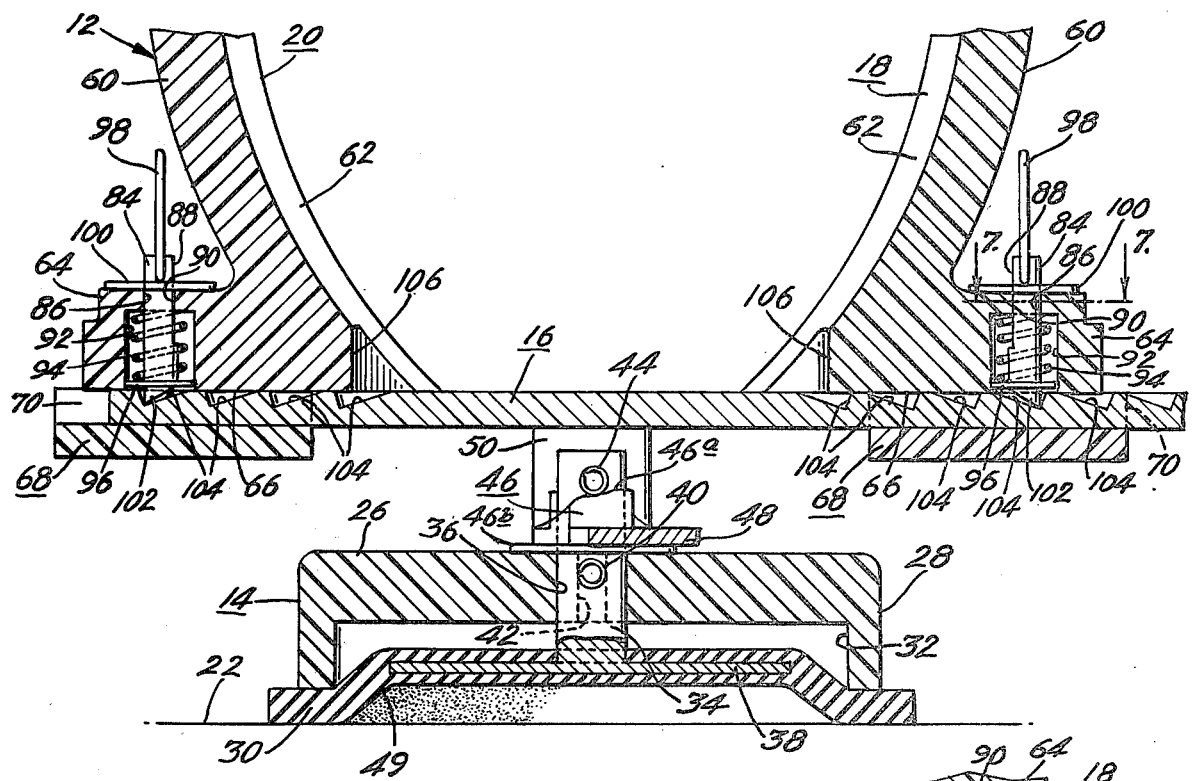
FIG. 4 is an enlarged sectional view taken along line 4—4 of FIG. 2.

Considering the details of the device, the suction cup assembly 14 as shown most clearly in FIG. 4 comprises a rigid cup 26 which includes a downwardly depending cylindrical side wall 28 terminating in engagement with a circular resilient diaphragm 30 having a diameter somewhat larger than that of said cup. The cup 26 and diaphragm 30 define therebetween a chamber 32 into which the diaphragm is drawn by a suitable actuating means.

Figure 5:
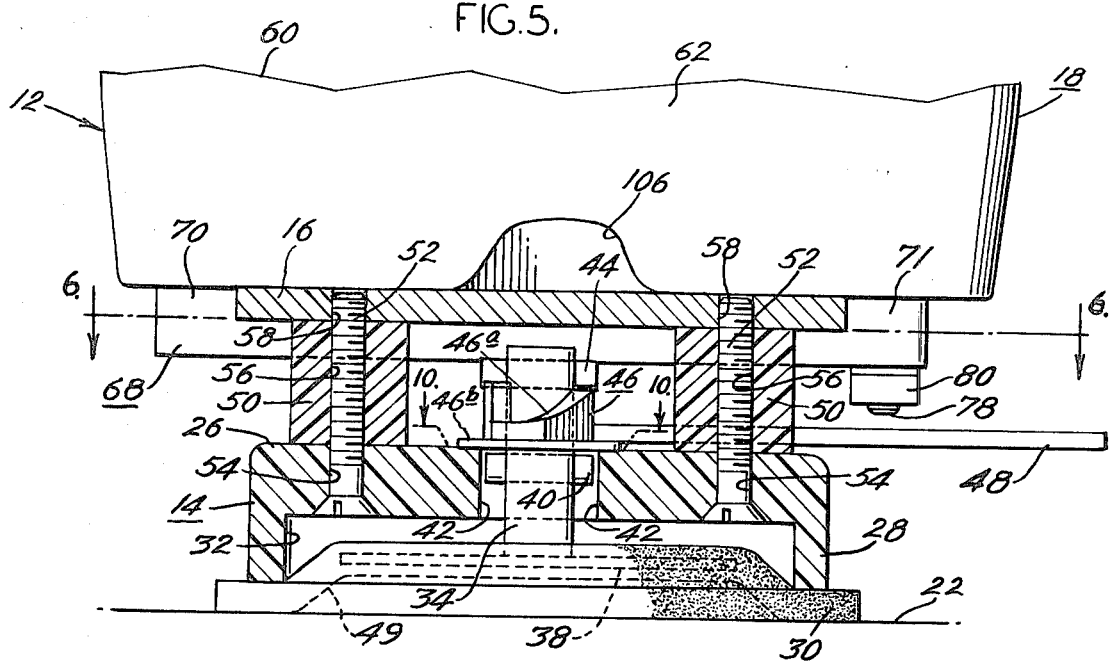
FIG. 5 is an enlarged sectional view taken along line 5—5 of FIG. 5.
Figure 10:
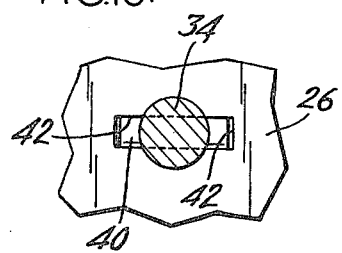
FIG. 10 is a sectional view taken along line 10—10 of FIG. 5.

The preferred diaphragm actuating means comprises a vertical shaft 34 slidable within a central bore 36 of the cup. The lower end of the shaft 34 terminates in an annular rigid plate 38 which is molded into the diaphragm 30. As shown in FIGS. 5 and 10, the shaft 34 is prevented from rotating with respect to the cup by a transverse pin 40 passing through the shaft, the ends of which slide in a slot 42 along bore 36 of the cup.

Figure 6:
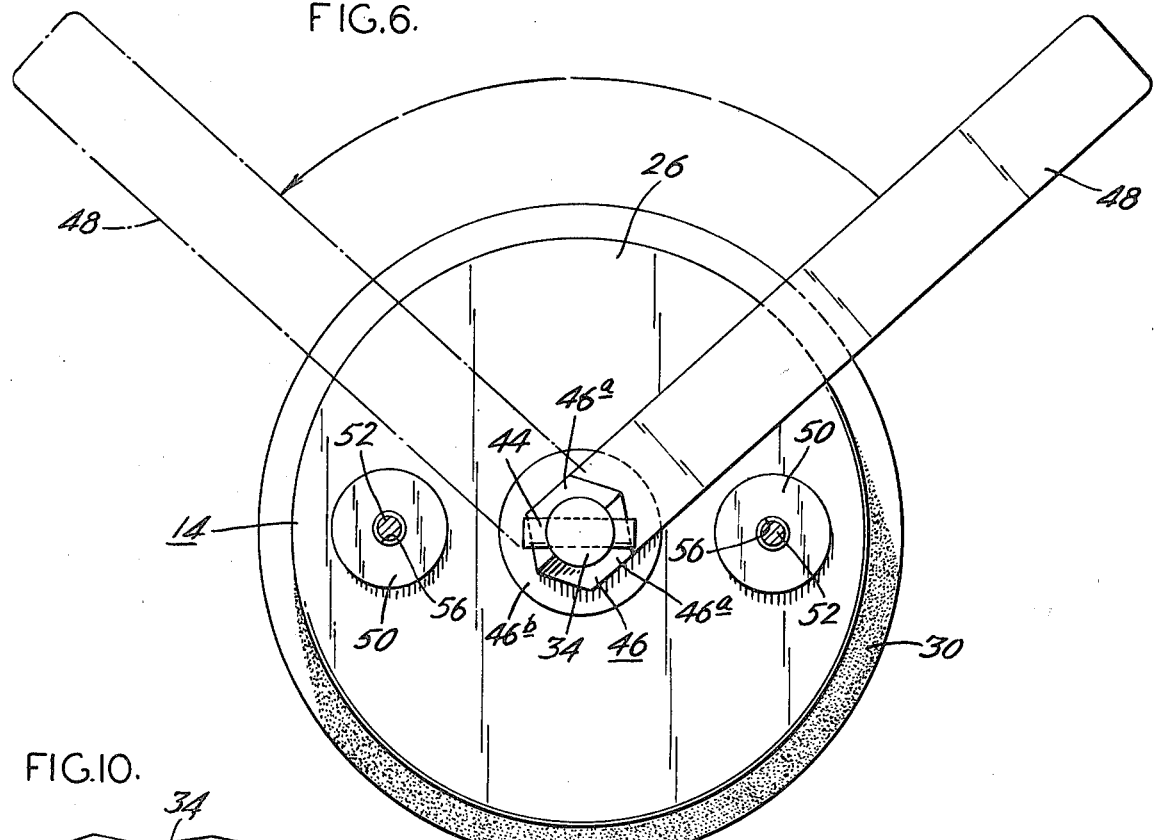
FIG. 6 is a sectional view taken along line 6—6 of FIG. 5 and showing in dot and dash lines the release position of the suction cup assembly actuating lever.

A second transverse pin 44 in the shaft 36 spaced above the top of the cup 26 cooperates with a cam element 46 which is selectively rotatable by means of cam actuating lever 48 extending therefrom. The projecting ends of the pin 44 ride on opposed identical cam surfaces 46a, each of which have essentially a ramp type configuration wih a plateau at the upper end thereof to support a pin end in the elevated position of the shaft 34. The cam element 46 rotates on a washer 46b seated on the top of the cup 26. A rotation of the actuating lever 48 through approximately 100° from the solid line position of FIG. 6 to the dot and dash line position will lower the shaft 34 and the diaphragm portion molded to the plate 38 thereof from the position shown in FIG. 4 to the release position wherein the diaphragm lower surface is a planar surface flush with the supporting table surface. The gripping effect of the suction cup assembly is in a conventional manner provided by the upward deformation of the resilient diaphragm which results in the formation of a vacuum cavity 49 between the table surface and the central portion of the diaphragm. The ambient air pressure in the chamber 32 acting upon the diaphragm in opposition to the low vacuum pressure in the cavity 49 provides the holding force which secures the vacuum cup assembly to the table surface.

Figure 2:
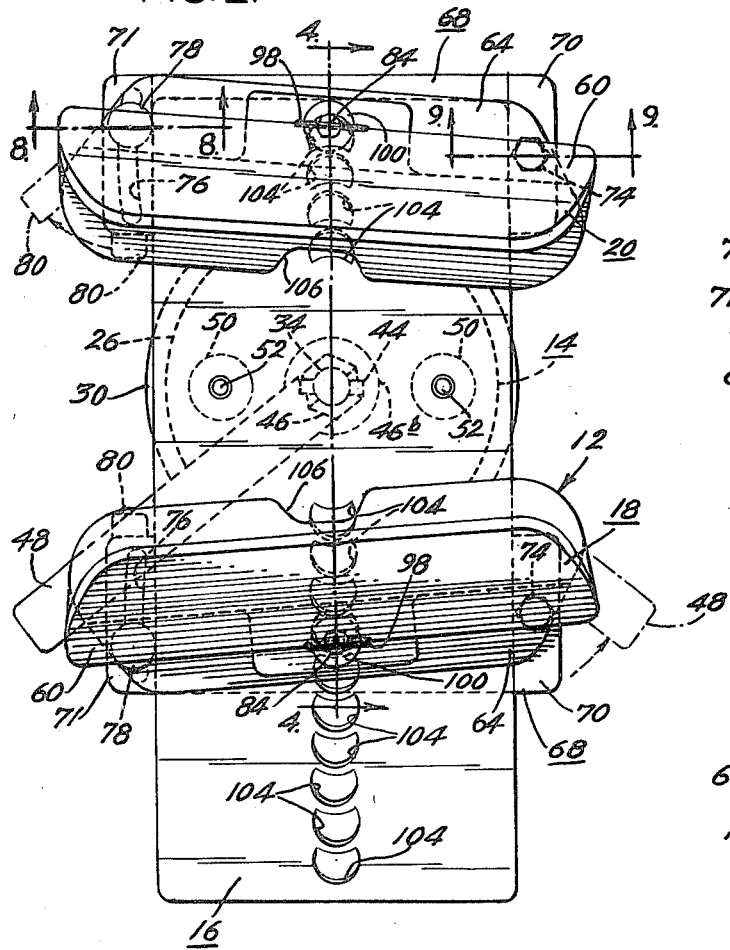
FIG. 2 is an enlarged plan view of the positioning device of FIG. 1 showing in dot and dash lines the release position of the suction cup assembly actuating lever and the adjusting position of one of the clamp assembly angle adjusting screw levers.
Figure 3:
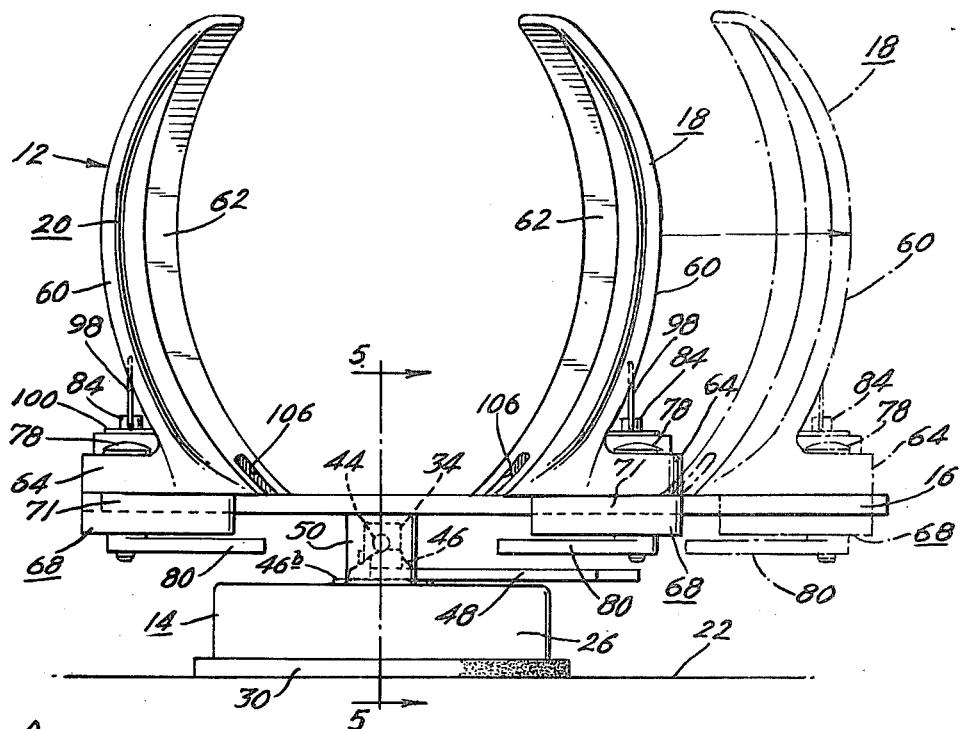
FIG. 3 is an end elevational view of the positioning device of FIG. 2 showing in dot and dash lines the extreme outward position of one of the clamp assemblies.

The limb support plate 16, which as shown in FIG. 2 is of an elongated rectangular shape, is preferably made of a strong but lightweight metal such as aluminum. The plate 16 is supported by the suction cup assembly 14 in spaced parallel relation to the table surface. As shown most clearly in FIG. 5, the support plate 16 rests on a pair of diametrically aligned cylindrical spacers 50 on top of the cup 26 and is secured to the cup by screws 52 passing through holes 54 in the cup, axial bores 56 in the spacers, and threaded holes 58 in the plate 16. The longitudinal centerline of the plate 16 extends perpendicularly to a plane passing through the spacers 50 and the shaft 34. As shown in FIGS. 2 and 3, the plate 16 is transversely centered above the suction cup assembly but extends substantially further longitudinally in the direction towards which the actuating lever 48 extends for reasons discussed herebelow.

The clamp assemblies 18 and 20 are identical in construction, one being the mirror image of the other. Accordingly, the same identifying numerals are used with respect to corresponding parts of the clamp assemblies. Each clamp assembly comprises a clamp member 60 which is preferably made of a molded plastic material and which has a generally arcuate configuration. The inwardly facing limb-engaging surface 62 of each clamp member 60 comprises a concave substantially cylindrical surface having a curvature diameter approximately corresponding to the average diameter of the type of limb to be clamped. In the case of a human thigh, the diameter of the clamp member curvature might suitably be 10 inches. The height of the clamp members should be such as to suffiently envelop the clamped limb so as to effectively restrain the limb against upward movement away from the support plate 16. The concave shape of the limb engaging surface 62 effectively carries out this function without the need for straps or other tie down mechanisms passing over the top of the secured limb.

The bottom of each clamp member 60 is characterized by an outwardly extending flange 64, the undersurface 66 of which rests on the support plate 16. The clamp member 60 and the flange 64 thereof have a length which is substantially greater than the width of the support plate 16. Since the clamp members are disposed transversely on the support plate 16, the ends of the clamp members extend beyond each side of the support plate as shown most clearly in FIG. 5. A guide member 68 underlying each clamp member is disposed beneath the support plate 16 and includes upwardly directed shoulder portions 70 and 71 at opposite ends thereof outboard of the plate 16 which engage the lower surface 66 of the clamp member. Each clamp member 60 is pivotally secured to its underlying guide member 68 at one end thereof by a bolt 72 passing upwardly through the shoulder 70 of the guide member and through the flange 64 of the clamp member. The bolt 72 is fastened by a cap nut 74 so as to allow pivotal movement of the clamp member with respect to the guide member.

Figure 8:
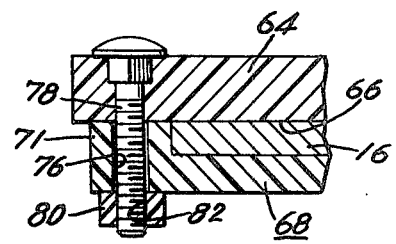
FIG. 8 is an enlarged sectional view taken along line 8—8 of FIG. 2 showing details of the clamp assembly angle adjusting means.
Figure 9:
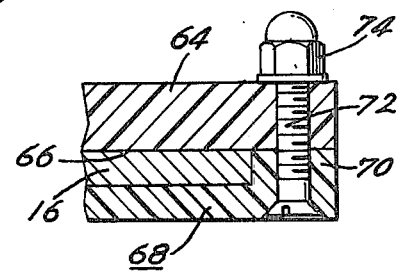
FIG. 9 is an enlarged sectional view taken along line 9—9 of FIG. 2.

The end of each clamp member opposed from its pivotally mounted end is adjustably secured to the guide member to permit a selective variation of the angle of the clamp member with respect to the support plate and with respect to the opposed clamp member. For this purpose, as shown in FIGS. 2 and 8, an arcuate slot 76 is provided on the shoulder 71 through which a carriage bolt 78 secured in the flange 64 freely passes. A clamp assembly angle adjusting lever 80 having a threaded bore 82 in one end thereof permits tightening the bolt 78 at any selected position in the slot 76. The guide members 68 are preferably made of a low friction plastic material such as Teflon to facilitate the sliding movement of the clamp assemblies 18 and 20 longitudinally along the support plate 16.

Figure 7:
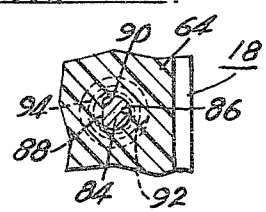
FIG. 7 is a sectional view taken along line 7—7 of FIG. 4 showing details of the clamp assembly adjustable locking means.

Means are provided for releasably locking each of the clamp assemblies in the desired longitudinal position on the support plate 16. In the preferred form of the invention, this means comprises a ratchet type locking arrangement characterized by a spring loaded pin carried by each said clamp member 60 which engages a series of underlying detents in the support plate. As shown most clearly in FIG. 4, the locking mechanism comprises a vertically disposed locking pin 84 passing through a bore 86 in the flange 64 of each clamp member. The pin 84 is flattened along an upper section 88 thereof and the bore 86 is provided with a corresponding flat section 90 as shown in FIG. 7 to prevent rotation of the pin. A spring chamber 92 within the flange 64 coaxial with the bore 86 contains a compression coil spring 94 bearing at its upper end against the top of the chamber 92 and at its lower end against a ring 96 attached to the pin 84 adjacent its lower end. The spring 94 will accordingly bias the pin in a downward direction, the pin being stopped by the engagement of a pull ring 98 passing through the upper end thereof with a washer 100 resting on the flange 64. The lower end 102 of the pin 84 is beveled inwardly toward the limb engaging surface of the clamp member.

A series of angularly inclined slots 104 as shown in FIGS. 2 and 4 are provided in the support plate 16 and are longitudinally aligned thereon with the pin 84 of the clamp members. To permit the reversibility of the clamp assemblies on the support plate, the slots 104 are preferably aligned on the longitudinal centerline of the support plate and the pins 84 are accordingly centered to cooperate with the slots. The slots 104 are cut in a generally saw-tooth pattern so as to present a gradually sloping ramp surface to the pin 84 as the clamp assembly is moved inwardly on the support plate 16, which in conjunction with the beveled lower end 102 of the pin permits ratcheting movement of each clamp assembly without the need to lift the locking pin pull ring 98. Movement of each clamp assembly outwardly along the support plate 16 is prevented by the nearly vertical outer walls of the notches 104 which engage the vertical side of the locking pin end 102. Accordingly, the outward movement of the clamp assemblies along the plate 16 can only be effected by first lifting the locking pin 84 by means of the pull ring 98 and holding the pin throughout the outward travel of the assembly. To prevent pinching of the patient's skin between the slots 104 and the leading edge of the clamp assemblies when the assemblies are advanced inwardly into a clamping position, notches 106 aligned with the slots 104 are provided in the limb engaging surface 62 of each of the clamp members 60.

For operation, the device is placed in the desired position on an examination table, and the suction cup assembly is actuated by moving the lever 48 from the release position to the locking position. As described above, this raises the diaphragm 30 in the manner shown in FIG. 4 to establish a differential pressure across the diaphragm, securing the assembly to the table surface.

To accept the limb to be secured, for example, the thigh of a patient, the clamp assemblies 18 and 20 are moved sufficiently far apart to permit the entrance of the patient's thigh therebetween. With the patient's thigh resting on the support plate 16, the device should be disposed with the actuating lever 48 and the longer length of the support plate 16 extending away from the patient, that is, on the outer side of the patient's leg. Prior to moving the clamp assemblies into a clamping position, the angle of each clamp member 60 may if necessary be adjusted by means of the angle adjusting lever 80 to accommodate the taper of the patient's thigh. With the appropriate angle established and the levers 80 turned to lock the clamp members in place on the guide members 68, the clamp assemblies 18 and 20 are positioned longitudinally on the support plate 16 simply by pushing one or both of the clamp members toward the patient's thigh until a firm contact of the limb engaging surfaces 62 with the thigh is produced. The clamp assemblies will automatically lock in place in the desired position by cooperation of the pins 84 with the slots 104 in the support plate. With the leg secured as described and as illustrated in FIG. 1, it will be apparent that the leg above the knee is effectively immobilized and that stress may be placed on the leg below the knee in any desired direction without danger of the thigh being displaced from the positioning device.

Upon completion of the examination, the patient's leg is released from the device simply by lifting the pull ring 98 of one of the clamp assemblies, usually the outermost one, and sliding the clamp assembly to an outward position such as shown in dot and dash lines in FIG. 3. The leg may then be lifted free of the device. If desired, the clamp assembly may be removed from the support plate to facilitate patient withdrawal, especially in the case of a painful leg condition.

In the event that both legs are to be examined, following examination of the first leg the device is released from the table and the clamp assemblies are interchanged on the support plate. The device is reattached to the table beneath the second leg with the actuating lever 48 and the elongated end of the support plate extending away from the patient, the device being rotated 180° from its former position. The transposition of the clamp assemblies provides the correct angular position of the clamp members without the need for readjustment of the levers 80. The outwardly directed position of the lever 48 and support plate longer end prevents interference of these elements with the patient's other leg.

The height of the support plate above the table surface is dependent on the length of the spacers 50 and this height can be varied as desired by selecting the appropriate spacer length to suit the use for which the device is intended.

The use of a single suction cup assembly permits the use of the device on any type of smooth-surfaced examination table, whether flat or of the curved type. The diaphragm is preferably made of a relatively stiff material to minimize the possible rocking of the device when stress is placed on the secured limb. A resilient synthetic material having a 40 durometer (Shore C) hardness has been found suitable in this regard while still providing sufficient grip on the table surface.

Although the ratchet type locking mechanism described is preferred for the clamp assemblies, other arrangements could suitably be employed; for example, a removable pin passing through a hole in each clamp member and selectively through one of a plurality of spaced holes in the support plate. The illustrated ratchet arrangement is advantageous in view of the speed with which a setup can be accomplished and the absence of seperable parts which could become lost or mislaid.

Although described primarily as a positioning aid for use in medical examinations, it will be apparent that the device can be usefully employed in other applications. For example, the device could be used by morticians during the embalming process to hold limbs of the body in any desired attitude. The device might similarly be employed be veterinarians to hold animals in a desired position, either for examination and X-ray photography, or for surgical procedures. In any of such uses, it will be obvious that more than one such device might be employed on the same table surface to position the same or different limbs of the secured subject.

Manifestly, changes in details of constructed can be effected by those skilled in the art without departing from the spirit and scope of the present invention.

I claim:

1. A positioning device for holding a human limb or the like in a fixed position above a table surface, comprising a rectangular elongated limb support plate, a single suction cup assembly attached to said support plate, said suction cup assembly providing means for selective attachment to a table surface to support said plate in parallel spaced relation to said table surface, a pair of opposed upstanding clamp assemblies disposed on said support plate, each of said clamp assemblies comprising a clamp member having a concave limb-engaging surface thereon, at least one of said clamp assemblies being slidably mounted on said support plate to permit selective movement thereof relative to the other said clamp assembly, means for adjusting the relative angular orientation of at least said slidable clamp assembly to accommodate the taper of a limb clamped therebetween, means for releasably locking said slidable clamp assembly in the desired position on said support plate, one end of said support plate extending substantially further beyond the suction cup assembly than the other end thereof, said slidable clamp assembly being adapted to slide along said extending end of said plate, said suction cup assembly comprising a rigid downwardly opening cup secured to said support plate, a resilient diaphragm extending beneath said cup, means for withdrawing said diaphragm partially into said cup to create a partial vacuum therebeneath and to secure said assembly to a table surface, said latter means comprising actuating means including an actuating lever disposed beneath said extending end of said support plate, and locking means for preventing rotation of said support plate and cup with respect to said diaphragm.

2. The invention as claimed in claim 1 wherein said diaphragm actuating means comprises a shaft attached to said diaphragm, a pin extending transversely through said shaft, and a ramp type cam attached to said actuating lever engaging said pin to raise or lower said shaft and diaphragm upon actuation of said lever.

3. The invention as claimed in claim 2 wherein said means for preventing rotation of said support plate and cup with respect to said diaphragm comprises a second pin in said shaft, said second pin being slidably movable within a slot in said cup to prevent relative rotation of said cup and said shaft.

4. The invention as claimed in claim 1 wherein said actuating lever is rotated in a plane parallel to said support plate to effect actuation of said suction cup assembly.

5. The invention as claimed in claim 1 wherein said means for releasably locking said slidable clamp assembly comprises a ratchet type locking arrangement permitting free inward movement of the clamp assembly toward a limb disposed between the clamp assemblies but preventing reverse movement thereof without release of a locking mechanism.

6. The invention as claimed in claim 5 wherein said ratchet locking arrangement comprises a spring loaded pin on said slidable clamp assembly, and a plurality of slots in said support plate adapted to cooperate with said spring loaded pin.

7. The invention as claimed in claim 1 wherein both of said clamp assemblies are slidably mounted on said support plate and angularly adjustable with respect to said plate.

8. The invention as claimed in claim 7 wherein each of said clamp assemblies includes a clamp member having a flange seated on said support plate, a guide member associated with each said clamp member disposed beneath said support plate and having shoulders at the ends thereof extending upwardly along said support plate and engaging the corresponding clamp member flange, means pivotally connecting one of said shoulders of each said guide member to said corresponding flange, means for selective angular adjustment and securement of the other of said shoulders to said flange to permit selective adjustment of the angle of said clamp member with respect to said support plate.

9. A positioning device for holding a human limb or the like in a fixed position above a table surface, comprising a rectangular elongated limb support plate, a single suction cup assembly attached to said support plate, said suction cup assembly providing means for selective attachment to a table surface to support said plate in parallel spaced relation to said table surface, a pair of opposed upstanding clamp assemblies disposed on said support plate, each of said clamp assemblies comprising a clamp member having a concave limb-engaging surface thereon, at least one of said clamp assemblies being slidably mounted on said support plate to permit selective movement thereof relative to the other said clamp assembly, means for adjusting the relative angular orientation of at least said slidable clamp assembly to accommodate the taper of a limb clamped therebetween, means for releasably locking said slidable clamp assembly in the desired position on said support plate, one end of said support plate extending substantially further beyond the suction cup assembly than the other end thereof, said slidable clamp assembly being adapted to slide along said extending end of said plate, an actuating lever disposed beneath said extending end of said support plate, and means operably connecting said actuating lever with said suction cup assembly for selective attachment or release of said assembly with respect to a table surface.

10. A positioning device for holding a human limb or the like in a fixed position above a table surface, comprising a limb support plate, a single suction cup assembly attached to said support plate, said suction cup assembly providing means for selective attachment to a table surface to support said plate in parallel spaced relation to said table surface, a pair of opposed upstanding clamp assemblies disposed on said support plate, each of said clamp assemblies comprising a clamp member having a concave limb-engaging surface thereon, at least one of said clamp assemblies being slidably mounted on said support plate to permit selective movement thereof relative to the other said clamp assembly, means for adjusting the relative angular orientation of at least said slidable clamp assembly to accommodate the taper of a limb clamped therebetween, means for releasably locking said slidable clamp assembly in the desired position on said support plate, said suction cup assembly comprising a rigid downwardly opening cup secured to said support plate, a resilient diaphragm extending beneath said cup, means for withdrawing said diaphragm partially into said cup to create a partial vacuum therebeneath and to secure said assembly to a table surface, said latter means comprising actuating means having an actuating lever disposed beneath said support plate, and locking means for preventing rotation of said support plate and cup with respect to said diaphragm.

11. The invention as claimed in claim 10 wherein said diaphragm actuating means comprises a shaft attached to said diaphragm, a pin extending transversely through said shaft, and a ramp type cam attached to said actuating lever engaging said pin to raise or lower said shaft and diaphragm upon actuation of said lever.

12. The invention as claimed in claim 11 wherein said means for preventing rotation of said support plate and cup with respect to said diaphragm comprises a second pin in said shaft, said second pin being slidably movable within a slot in said cup to prevent relative rotation of said cup and said shaft.

13. The invention as claimed in claim 12 wherein said actuating lever is rotated in a plane parallel to said support plate to effect actuation of said suction cup assembly.

* * * * *

UNITED STATES PATENT OFFICE
CERTIFICATE OF CORRECTION

PATENT NO. : 4,181,297
DATED : January 1, 1980
INVENTOR(S) : Thomas K. Nichols

It is certified that error appears in the above-identified patent and that said Letters Patent are hereby corrected as shown below:

Column 3, line 52 change "wih" to --with--.

Column 7, line 14 change "be" to --by--.

Column 10, line 14 (Claim 13) change the numeral "12" to --10--.

Signed and Sealed this

Eighteenth Day of March 1980

[SEAL]

Attest:

SIDNEY A. DIAMOND

Attesting Officer

Commissioner of Patents and Trademarks